(12) United States Patent
Jain

(10) Patent No.: US 11,379,966 B1
(45) Date of Patent: Jul. 5, 2022

(54) IMPURITY DETECTION SYSTEM IN CONTINUALLY RUNNING WATER THROUGH MACHINE VISION SOFTWARE

(71) Applicant: Alisha Iyer Jain, Los Altos, CA (US)

(72) Inventor: Alisha Iyer Jain, Los Altos, CA (US)

( * ) Notice: Subject to any disclaimer, the term of this patent is extended or adjusted under 35 U.S.C. 154(b) by 0 days.

(21) Appl. No.: 17/699,138

(22) Filed: Mar. 20, 2022

(51) Int. Cl.
*G06K 9/00* (2022.01)
*G06T 7/00* (2017.01)
*G06T 7/90* (2017.01)

(52) U.S. Cl.
CPC .............. *G06T 7/0002* (2013.01); *G06T 7/90* (2017.01); *G06T 2207/10016* (2013.01); *G06T 2207/10024* (2013.01)

(58) Field of Classification Search
CPC ............ G06T 7/0002; G06T 7/90; G06T 2207/10016; G06T 2207/10024; C02F 1/043; C02F 1/006; C02F 1/46104; C02F 1/32; C02F 1/78; C02F 1/72; C02F 2103/02; C02F 2103/04; C02F 2201/32; C02F 2209/00; C02F 2209/001; C02F 2209/003; C02F 2301/00; C02F 2303/00; C02F 2303/18; C02F 2305/00; H04M 1/72403; H04M 2250/52

See application file for complete search history.

(56) References Cited

U.S. PATENT DOCUMENTS

| | | | |
|---|---|---|---|
| 6,524,447 B1 * | 2/2003 | Carmignani | B01J 35/002 210/748.14 |
| 8,472,661 B2 | 6/2013 | Bick | |
| 9,809,468 B1 | 11/2017 | Jain | |
| 10,817,725 B1 | 10/2020 | Jain | |
| 2005/0009192 A1 * | 1/2005 | Page | G01N 33/1886 422/62 |
| 2006/0207431 A1 * | 9/2006 | Baca | A61L 2/24 96/224 |
| 2016/0327473 A1 * | 11/2016 | Ozcan | H04N 5/23293 |

* cited by examiner

*Primary Examiner* — Duy M Dang
(74) *Attorney, Agent, or Firm* — Stephen E. Zweig

(57) ABSTRACT

System and method of implementing an Impurity Detection System in Continually Running Water employing spatially separated smartphone video cameras equipped with periscopic lens attachments, a water flow meter, a sensor operated reagent dispensing system, a light reflecting chamber with patterned surface and optically transmissive windows, and machine vision software for image analysis. The smartphone is equipped with custom optical lens attachments including a periscope that improves spatial separation between camera images. The water flow meter bends according to the amount of water flow, and the sensors modulate the amount of dispensed reagents, such as orthotolidine ($C_{14}H_{16}N_2$). The apparatus monitors the varied levels of impurities, including turbidity and fluorescence, within continually running water, and triggers alarm signals. Machine vision software subsequently analyzes the spatially separated images and matches existing databases to identify key contaminant characteristics.

16 Claims, 7 Drawing Sheets

IMPURITY DETECTION SYSTEM IN CONTINUALLY RUNNING WATER THROUGH MACHINE VISION SOFTWARE

BACKGROUND OF THE INVENTION

Field of the Invention

This invention is in the field of water quality monitoring systems and methods

Description of the Related Art

Although we often take access to safe drinking water for granted, there is a lot of complex science and engineering behind our water supply. Although large amounts of fresh water exist in lakes, rivers, and streams, this water is frequently contaminated. These contaminants include suspended solid particles, which in turn carry harmful bacteria and other pathogenic microorganisms. The contaminants also contain various harmful chemicals as well.

Affluent societies have many sophisticated chemical methods to test water, as well as many large-scale methods to purify water. These large-scale purification methods include large civil engineering structures such as reservoirs, coagulation, filtration and disinfection facilities. Usually, the incoming water is first tested to determine the type and concentration of contaminants that need to be removed. Additional testing is often done during the purification process, and at the end, the final product must again be tested to ensure that the water is now safe for use. Thus, water quality testing (e.g., testing for various types of contaminants) is important throughout this process.

Such large-scale systems are not always available, however. Even affluent societies can be impacted by war and natural disasters that can knock out such advanced water treatment facilities. Less affluent societies and persons in wilderness areas may struggle to obtain any type of water. Thus, there is a need for rapid and inexpensive methods to both test and purify water on a smaller scale basis.

Many small-scale water test methods are known. Some systems, exemplified by Bick, U.S. Pat. No. 8,472,661, the entire contents of which are incorporated herein by reference, make use of smartphones to help streamline certain aspects of the analytical process. Such prior art systems typically place a measured amount of water into a container, add one or more test chemicals to the container, and then analyze for color changes or turbidity changes. The water sample is often then discarded.

Small-scale water purification systems are also known. Such systems include the photochemical sterilization systems Jain, U.S. Pat. No. 9,809,468, the entire contents of which are incorporated herein by reference. Other methods include chemical disinfection tablet systems, filtration systems and others.

BRIEF SUMMARY OF THE INVENTION

The invention is based, in part, on the insight that most water purification systems, even small-scale systems often operate on a continuous basis. The invention is also based on the insight that most small-scale water purification systems can only manage a range of certain water impurities. If they are presented with intake water with an unexpectedly high level of a given impurity, the water purification system may produce impure water. Such small-scale water purification systems can also break unexpectedly as well.

Thus, at least for small scale-water purification purposes, what is needed is an inexpensive water test system that can operate on a continual basis, preferably on an automatic or semi-automatic basis. Such a continuous water analysis system can be positioned to continually monitor intake water before a small-scale water purification system. This system could sound an alarm, or even shut off water to a purification plant, if the level of contaminants in the intake water was unexpectedly high. Such a continuous water analysis system can also be positioned to continually monitor the output from a water purification plant. This too can be configured to automatically sound an alarm or shut off water if the water purification plant unexpectedly failed.

As will be discussed, the present disclosure teaches an inexpensive, small-scale, water test system and method that can operate for long periods of time on an automatic or semi-automatic basis. Unlike most prior art systems, which rely upon scooping up small amounts of water and testing the water in containers, the present art teaches a continual flow test system where water continually flows through the apparatus. The apparatus is configured with a reagent dispensing system and a smartphone based computerized analysis and control system. The smartphone monitors the rate of flow of water through the system, and also directs application of test chemical reagents to the water as it is transiting the apparatus. Video cameras on the smartphone monitor the progress of the chemical reaction, and the smartphone processor computes the level of impurities based on the observed reaction. The reacted chemicals exit the system, new intake water comes in, and the process can repeat for as long as desired. The results from the analysis can be coupled to alarm systems or water control valves so that problems can be quickly detected and corrected.

BRIEF DESCRIPTION OF THE DRAWINGS

FIG. 4B also shows an earlier reaction zone about to exit the chamber.

DETAILED DESCRIPTION OF THE INVENTION

The invention may be a system, apparatus, and method of analyzing running water for impurities. Although the invention will often be described as a method, the system and apparatus forms of the invention are not disclaimed. Indeed, it will often be convenient to describe at least portions of the invention in apparatus form.

Figure 1:
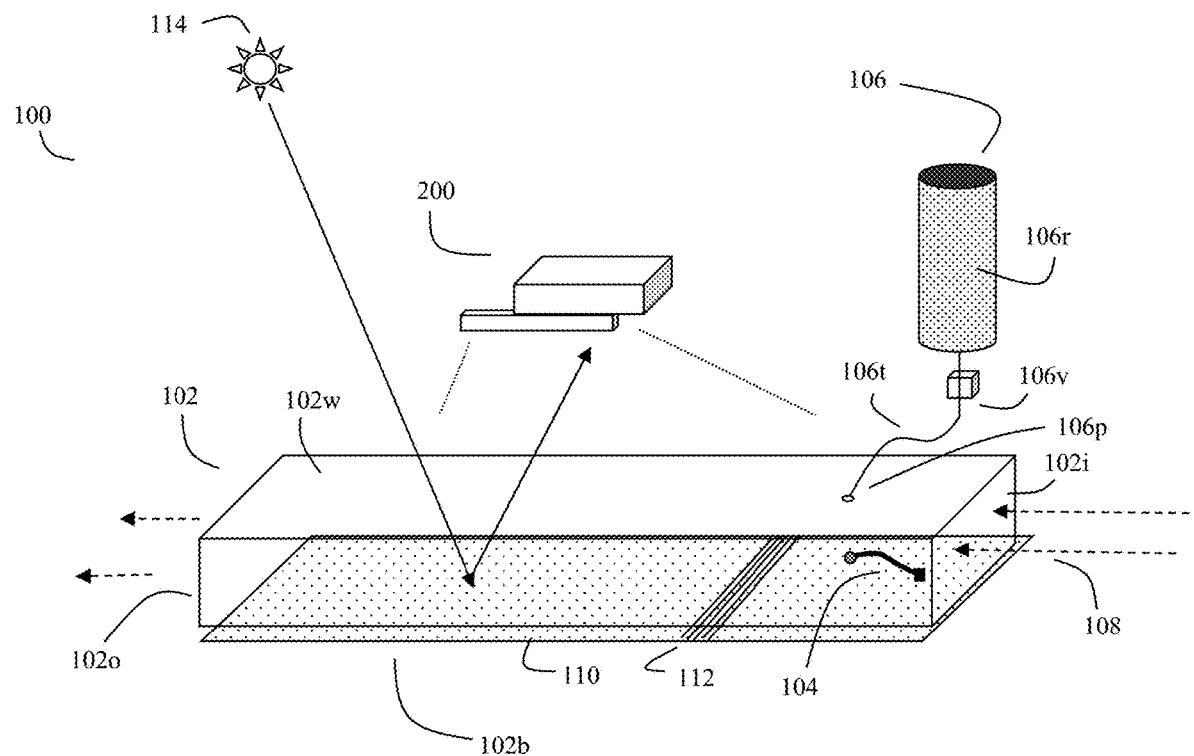
FIG. 1 shows an overview of the invention's apparatus. Here a hollow chamber with a transparent top, a running water inlet, and a running water outlet is placed in the water. A reagent dispensing system, here filled with a test reagent, is set up to administer the test reagent.

FIG. 1 shows an overview of an apparatus that can be used to implement the present invention. Here chamber (100), which can a glass or plexiglass chamber, with a transparent top (102w), a running water inlet (102i), and a running water outlet (102o) is placed in the water (108). A reagent dispensing system (106, 106v, 106p, 106t), here filled with a test reagent (106r), is set up to administer the test reagent.

In this example, the chamber has only four solid sides, with the sides corresponding to the chamber inlet (102i) and the running water outlet (102o) being completely absent. Thus, when immersed in a river or stream, at least a portion or "sample" of the stream's running water (108) can pass through the chamber without resistance at essentially the same flow rate as the rest of the stream. In this way, the invention can continually get an accurate sample of the stream, and continually monitor the running water in the stream for desired impurities.

This reagent dispensing system will typically comprise at least a reagent storage container (106), a pump or valve (106v), tubing (106t), and often a reagent administration port (106p). Here for simplicity, a simple gravity feed drip type system is shown. The rate of flow of reagent (106r) into the chamber (102) can be controlled by either manually or automatically adjusting valve (106v).

Note that by using multiple systems (100), but with different reagents (106r), multiple analytes in a given stream may be simultaneously measured.

The rate of water flow through the chamber can be measured with a water flow meter (104), and the test can be continually monitored using one or more digital video cameras. In a preferred embodiment, the digital video cameras are smartphone (200) digital video cameras. This smartphone embodiment will be discussed in more detail shortly.

Many different types of water flow meter may be used. These can comprise electronic water flow meters, mechanical water-wheel type flow meters, and other types of water flow meters. In this example, for simplicity, a simple ribbon of material (104), attached to the bottom (102b) of the chamber on one end, and with a small float on the other end is shown. A higher rate of water flow (108) will cause the ribbon and float to be displaced towards the outlet (102o), while a lower rate of water flow will cause the ribbon and float to tend to go straight up. As will be discussed shortly, the smartphone can photograph this mechanical flow meter (104), and use its image to calculate water flow.

Put alternatively, and as previously discussed, in some embodiments, the invention may be a method of analyzing running water (108) for impurities. This method typically comprises placing a chamber (100) comprising an inlet (102i), an outlet (102o), and at least one optically transmissive window (102w) in said water so that at least some of said water, comprising a sample of said water, enters said inlet (102i), transits past said optically transmissive window (102w), and exits said outlet (102o) while continuously flowing through said chamber (100).

As shown in FIG. 1, chamber (100) will usually further comprise a bottom that will usually also comprise a light reflective background (102b). This is usually disposed underneath the optically transmissive window (102w). Bottom and light reflective background is usually configured so that the running water (108) runs between the optically transmissive window (102w) and the light reflective bottom and background (102b) while the water (108) is running through the chamber (100).

The camber will also further comprise a water flow meter (here a mechanical water flow meter 104 is shown). This water flow meter will produce a signal, such as a visible signal, that indicates how fast the water (108) is flowing through the chamber. FIG. 1 also shows that the light reflecting background (102) can comprise various regions (or at least one region) with different light reflecting characteristics. Here, the light reflecting background (102) comprises one region (110) with a first defined light reflecting characteristic and another region (112) with a different defined light reflecting (optical) characteristic.

As can be seen in FIG. 1, the chamber further comprises at least one reagent (water test chemical) dispensing system (here shown as 106, 106v, 106p). This reagent dispensing system is configured to automatically administer, at a controlled rate, at least one reagent (106r) into the water sample (e.g., water within the chamber at that given time) while the water (108) is passing through the chamber (100).

Adjusting the rate of administration of test chemicals:

The flow meter (104) has multiple users. In addition to providing critical information as to the amount of water that is passing through the chamber, the flow meter can be also used to help determine how quickly to administer the test chemicals (reagents) to the chamber.

To do this, a computer processor (such as the smartphone's computer processor) and the signal from the mechanical flow meter (104) can be used to configure how fast the reagent dispensing system (106, 106v, 106p) should dispenses the test reagent into the chamber. For example, the flow rate of reagents into the chamber can be controlled by fluid valve (106v). If the water flow rate (108) is high (above a preset limit), the system may determine that more reagents (106r) are needed, and thus that the valve (106v) should be opened more. Conversely, if the water flow rate is low (below a preset limit), the system may determine that a smaller amount of reagent (106r) is needed, and thus that the valve (106v) should be opened less. Alternatively, in situations where 106v is a pump, the computer processor can control the speed of the pump.

As will be described in further detail later in this disclosure, the at least one reagent (106r) is usually selected to induce a change in the optical characteristics of the sample of said water in response to at least one impurity in said water. In the case where the water flow (108) is intended for drinking purposes, these impurities will be impurities that can either interfere with the potability of the water. Alternatively, when the water (108) is intended for further purification downstream, the system may monitor for impurities that might interfere with a subsequent purification step. When the water is intended for agricultural or industrial purposes, impurities that might interfere with plant growth, or a particular industrial process, might be monitored using alternative test reagents and methods.

Regardless of the choice of test reagent (106r), the invention typically operates by exposing the chamber to a light source (114). This light source might be the sun (e.g., natural light), may also be artificial light. This artificial light may include any of visible light, ultraviolet light, or infrared light depending on the test reagents contemplated. In either event, the light reflects off said light reflecting background (102b), passes through at least some of the water (108), and exits the optically transmissive window (102w). It is then imaged by the smartphone video cameras (200).

The light reflecting background (102b) will often comprise a white matte surface (110) selected to reflect light uniformly over a plurality of angles. Other types of reflecting backgrounds may also be used.

Smartphone (200) is exemplified by the popular Apple iOS or Android series of smartphones. Such smartphones typically have at least one computer processor (often based on the popular ARM series of computer processors), multiple gigabytes of RAM and Flash memory, touch sensitive display screens, and often two or more spatially separated video cameras.

In a preferred embodiment, the invention uses the smartphone's two (or more) spatially separated video cameras to simultaneously obtain images, over a plurality of locations along the optically transmissive window (102w), and a plurality of times while the water (108) is flowing through the chamber. Here a "plurality of locations" simply means that the cameras are imaging multiple regions through the chamber window (102w), including at least regions surrounding the sample application port (106p) as well as portions of reflecting backgrounds (110) and (112). As well as regions surrounding the flow indicator (104).

Similarly, the "plurality of times" simply means times spanning at least the times before, during, and optionally after the automatic administration of the reagent (106r) to the chamber. Typically, so that stereo imaging techniques may be used, the smartphone will produce color video images from at least two different camera angles these various locations as seen through the optically transmissive window (102w).

Figure 5:
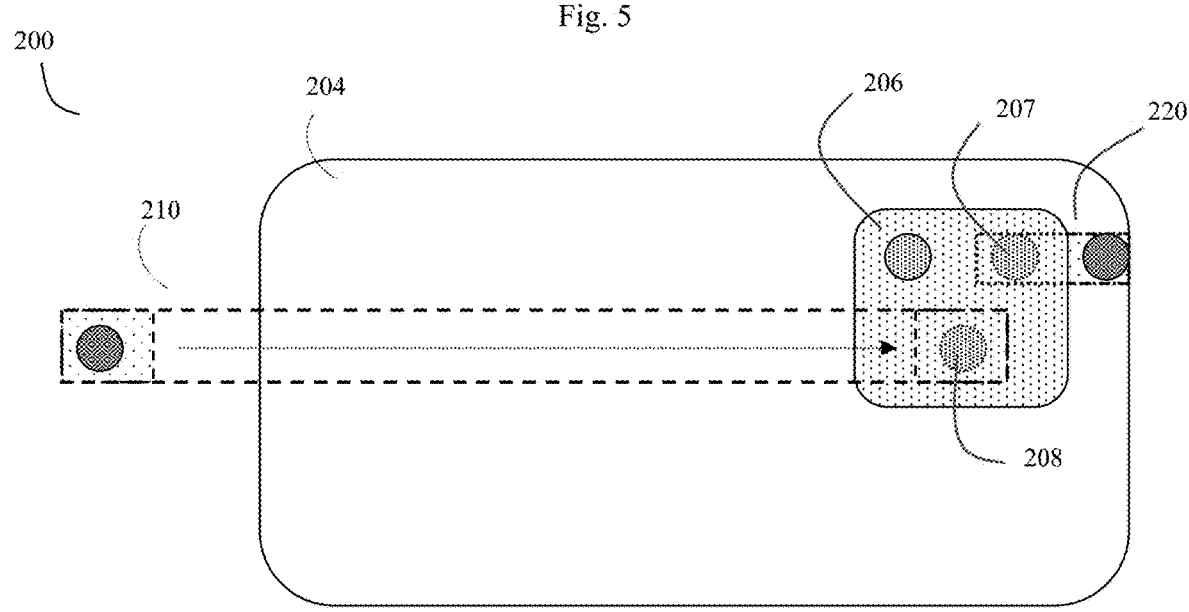
FIG. 5 shows an example of a modified smartphone and smartphone video camera system that can be used to image the invention's water flow apparatus.
Figure 5A:
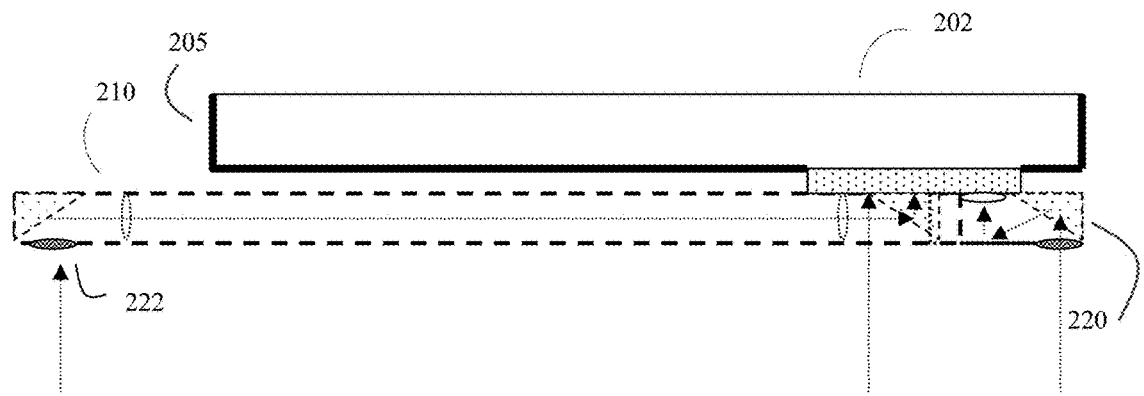
FIG. 5A is a top view of the smartphone system previously shown in FIG. 5.

An example of a preferred type smartphone device, such as an Apple iPhone 10 or later, is shown in FIG. 5 and FIG. 5A. In a preferred embodiment, the smartphone (200) will further comprise at least two spatially separated video cameras (such as 206, 207, and 208) and at least one lens attachment, such as periscopic attachment (210). In FIG. 5, this periscopic attachment is shown mounted on the back (204) of an Apple iOS 12 pro smartphone (205). The front of the smartphone, which may have a display screen, is shown as (202). Other arrangements may also be used.

This lens attachment (210) may be configured to create either an enhanced spatial separation between at least two of the spatially separated video cameras (see how attachment 210 acts like a periscope). It can also supply a different optical filter between the spatially separated cameras, or in some embodiments, both. In some cases, additional light analysis devices, such as spectroscopes, (220), or additional optical filters, may also be mounted on any additional video cameras, such as 207.

As will be discussed, in a preferred embodiment, the invention will use at least one processor, such as the smartphone processor, to analyze the color video images from these spatially separated video cameras (e.g., 206, 208, and possibly 207), to determine how the least one reagent (106r), reacts with impurities in the water. To do this, as previously discussed, the system takes image data from various locations along the optically transmissive window (102w) at a plurality of times. The invention will use this data (changes in the optical characteristics of this sample of water), suitable image analysis software such as machine vision software, and other information (such as algorithms correlating the reagent type and optical changes to levels of impurities) to determine the type of impurities in the water, as well as the concentration (or amount) of that impurity in the water. Examples of such machine vision software include Matlab, OpenCV, SimpleCV, Tensorflow, and other systems. See FIG. 7 for more detail.

Figure 1A:
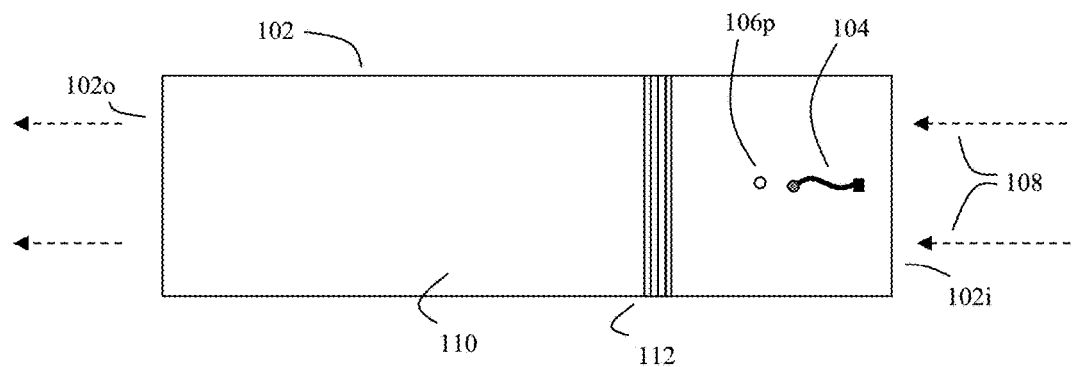
FIG. 1A shows an image of the running water, here illuminated by sunlight though the transparent top window, through the water transiting the chamber, reflecting off the light reflecting background on the bottom of the chamber, as seen by the smartphone video cameras.

FIG. 1A shows an image of the running water (108), here illuminated by sunlight (114) though the transparent top window (102w), through the water transiting the chamber, reflecting off the light reflecting background (102b) on the bottom of the chamber, as seen by the smartphone video cameras (200). In this embodiment, one region of the reflecting background contains a plurality of optical targets (112) to assist in the analysis. Another region (110) contains a different type of reflecting background, such as a matte white background.

Figure 2:
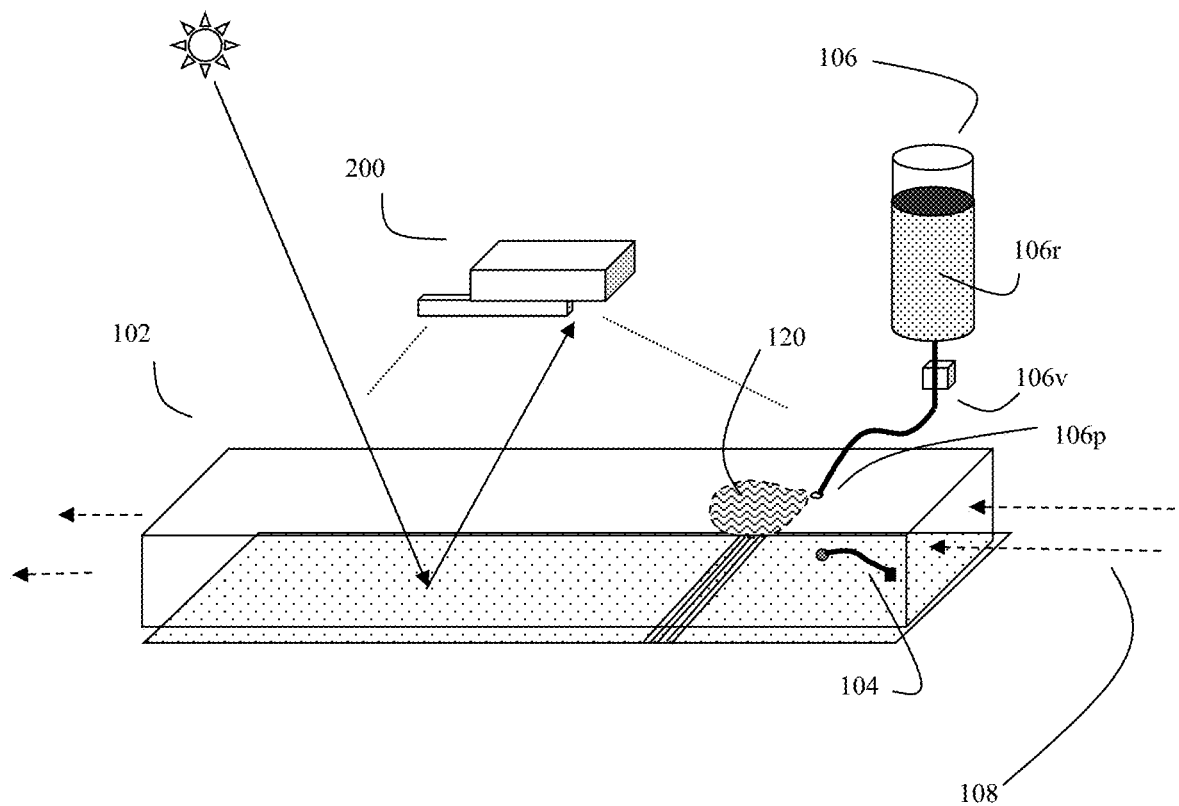
FIG. 2 shows the apparatus in action. As the water flow indicator bends according to the amount of water flow. The smartphone cameras read the indicator, compute the amount of water flow, and then compute how much test reagent to administer.

FIG. 2 shows the apparatus (100) in action. In this embodiment, the water flow indicator (104) bends (or otherwise changes position) according to the amount of water flow. Cameras on the smartphone (200) image the water flow indicator (104). The smartphone's processor or other computer processor computes the amount of water flow, and then computes how much test reagent (106r) to administer. This information (amount of test reagent to add) is used to adjust the valve (106v) on the reagent dispenser. The reagent dispenser adds test reagent to the chamber (here through port 106p). The test reagent (106r) reacts with impurities in the water, resulting in a change in the color, turbidity, fluorescence, or other type of optical characteristic (120) in the reaction zone. This is called an "optical signal". This optical signal in this reaction zone (120) in turn is imaged by the smartphone's cameras.

Figure 2A:
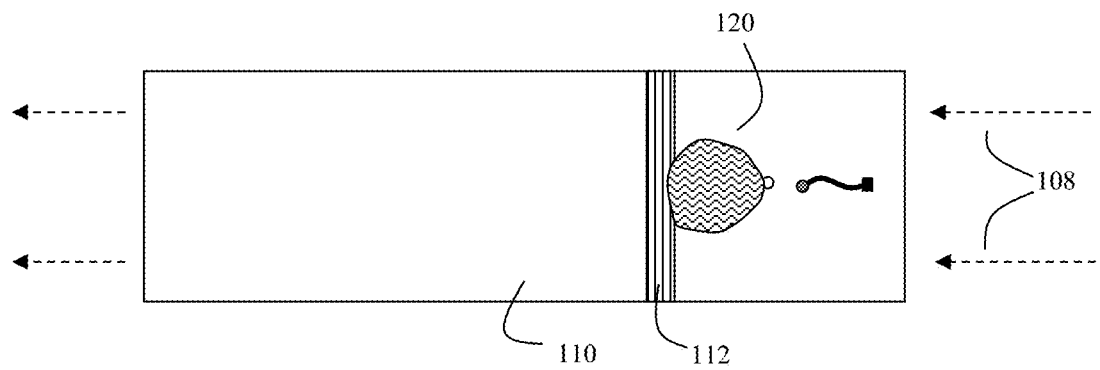
FIG. 2A shows an image of the apparatus as seen from the smartphone's perspective. Here, the reagent has reacted with an impurity in the running water, resulting in a color change or turbidity change.

FIG. 2A shows an image of the apparatus from FIG. 2 above, as seen from the smartphone's perspective. Here, the reagent (106r) has started to react with an impurity in the running water, resulting in a color change or turbidity change type optical signal in the reaction zone (120). In this figure, the reflective background (102b) has both a white matte surface (110), and also a patterned surface (112) to help the system determine turbidity. In this example, the white surface (110) is useful for clearly measuring the size and optical change of the reaction zone (120), while the patterned surface (112) is useful for estimating the turbidity in the reaction zone (120) as compared to the same water sample outside of the reaction zone.

Various types of test reagents:

Some water impurity test reagents, such as orthotolidine, operate by causing a change in the color or fluorescence of the reacted sample of water (120) in response to a fully dissolved impurity (often ionic impurities). These can comprise any of chlorine, arsenic, heavy metal, or nitrate type impurities. Here, the light reflective background (102b) will often have at least one region with a light reflecting background (such a matte white background 110) that is selected to facilitate detection of this change in color or fluorescence.

Note that while white is often used as an example, here, for alternate reagent systems, alternate types of backgrounds may be appropriate. Indeed, if fluorescent reagents are used, such as resorufin b-D-glucronide (used for detecting E. coli), even use of an ultraviolet light source and a black background (110) may be appropriate.

Typically, the at least one processor is configured to determine at least one amount and type of impurity by analyzing color video images of chamber locations both upstream of the reacted reagent (120), and downstream of the reacted reagent (120). Here, the system will typically determine differences in at the colors of the color video images between those locations upstream and downstream of the reacted reagent (120). This is shown in more detail in FIG. 6 and FIG. 7.

Figure 3:
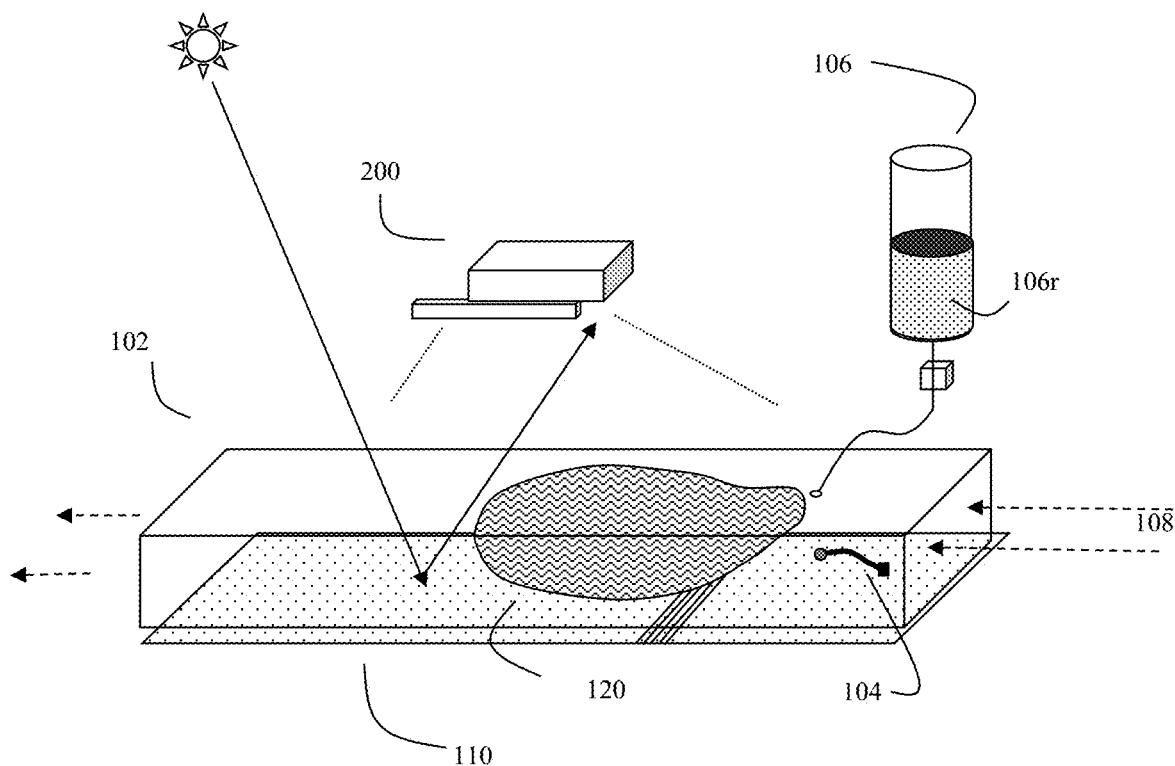
FIG. 3 shows how as more reagent is dispensed into the running water; the size of the reaction zone increases. The smartphone can use information regarding the size and intensity of the optical reaction, knowledge of the reagent type, water flow, and dimensions of the chamber to compute the approximate concentration of a given type of impurity in the water.

FIG. 3 shows how as more reagent (106r) is dispensed into the running water; the size of the reaction zone increases (120). The smartphone can use information regarding the size and intensity of the optical reaction, knowledge of the reagent type, water flow, and dimensions of the chamber to compute the approximate concentration of a given type of impurity in the water.

Figure 3A:
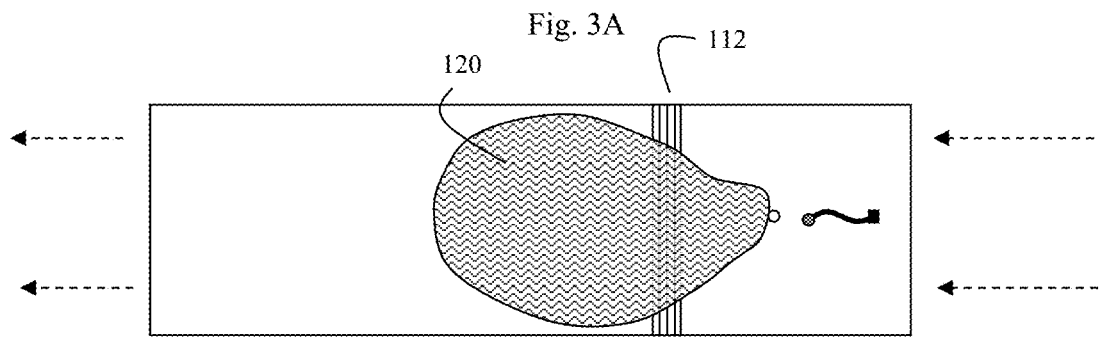
FIG. 3A shows how, in some embodiments, the reflective background may also comprise various optical targets.

FIG. 3A shows how, in some embodiments, the reflective background may also comprise various optical targets. In this example, assume that the reagent (106r) is a flocculant chemical, such as alum, or a high molecular weight polymer such as polyethylene oxide or polyacrylamide, which causes water suspended particles (solids, colloids) to form larger aggregates, resulting in an increase in turbidity. This turbidity can be measured optically by looking at how much the optical targets (112) become obscured, as well as by comparing the amount of light scattering between two smartphone video cameras (for example, FIG. 5 210-208, and 206) at different angles.

In some embodiments, the improved measurements of the reaction zone (120) can be done using different video cameras (such as 206, 208) using different optical filters (no filter for camera 206; filter 222 for camera 208). These optical filters can be selected to either preferentially absorb or preferentially pass wavelengths of light corresponding said at least one reagent's (106r) change in color. The smartphone processor in turn can retrieve information pertaining to the reagent (106r) and filter (222) from memory, and use video information obtained through the various cameras and optical filters to further analyze the color images.

As previously discussed, in some embodiments, the at least one reagent (106r) may be a flocculant, chosen to induce a change in the turbidity of the reaction zone (120) in response to suspended solids or colloids in the water. Here, the light reflective background (102b) may have one or more regions (110, 112) selected to optimize turbidity detection.

Here, for example, the at least one computer or smartphone processor can be configured to analyze color video images of locations both upstream of the reagent reaction zone (120) (the 102i side of the reaction zone 120), and downstream of the reagent reaction zone (the 102o side of reaction zone 120). The processor can then determine differences in the opacity of the color video images between those various locations.

To facilitate this process, in at least some embodiments, the light reflective background (102b) may contain a plurality of optical targets (112) chosen to become progressively harder to resolve as turbidity increases. These targets can be selected to be much like a photo resolution test chart, such as an I3A/ISO 122233 resolution test chart, or other camera resolution test, and can contain a series of lines with progressively finer specification. As the turbidity increases, the lines will become progressively harder to resolve, and the processor can be calibrated to relate the disappearance of certain lines with a given level of turbidity.

Alternatively, in some embodiments, the light reflective background (102b) can comprise a plurality of reflective areas (here again shown as 112). These reflective areas can be configured to reflect the incident light (114) through the reaction zone (120) at a plurality of different angles. The light beam from each different reflected angle will travel a different distance through the turbid reaction zone (120). As a result, each different light beam angle will travel a different distance through the reaction zone (120) sample of water, and will be is attenuated by the turbidity of the reaction zone by a differing extent. Here again, the computer processor can be configured to monitor the output from the various video cameras, and correlate the results with a given level of turbidity.

For this later application, in a preferred embodiment, the lens attachment (FIG. 5, 210) is ideally configured to create a spatial separation of at least six inches between the spatially separated video cameras (206, 208). In some embodiments, 210 may be a telescoping lens attachment that can be configured to provide a variable spatial separation.

Here again, the system will be configured to use the at least one processor to analyze the color video images from the various spatially separated video cameras. The system will then determine, based on the at least one reagent (106r), and images of the various locations along the optically transmissive window (102w) at various of times (such as before and after administration of reagent 106r), at least one amount (quantity, concentration) of suspended solids or colloids in the water.

Thus, for example, if reagent (106r) is a non-turbid flocculant, such as a polymer, and the water 108 before addition of reagent is also clear, then before the reagent is added to the water, the area surrounding target (112) should be clear, and the video cameras should resolve fine details in the target. If, however, upon hitting the water, the reaction zone (120) becomes turbid (see FIG. 3A), obscuring at least some of the details of the target (112), the system can conclude that the water 108 contained a possibly unacceptable level of suspended solids.

As a further example, in some embodiments, the light source (114) can be sunlight, and the at least one reagent (106r) can comprise a flocculant, such as alum, or polymer that has been selected to accelerate a rate of flocculation of any suspended solid or colloidal impurities in the water (108). This in turn causes an increase in turbidity in the reaction zone (120) and other portions of water downstream of the reagent administration port (106p).

Figure 4:
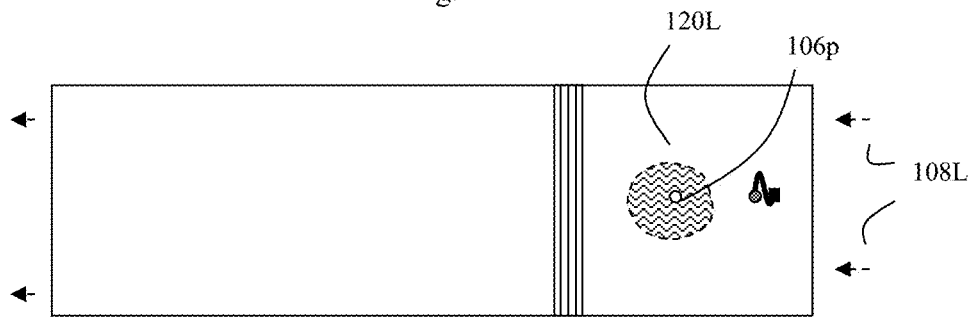
FIG. 4 shows how the system can operate at low water flow rates. Here the mechanical flow meter is not displaced downstream by the running water. Similarly, the region of color change caused by any dispensed reagent remains dispersed around the reagent inlet port.

FIG. 4 shows how the system can operate at low water flow rates (108L). Here the mechanical flow meter is not displaced downstream by the running water. Similarly, the region of color change (112L) caused by any dispensed reagent remains dispersed around the reagent inlet or port (106p).

Figure 4A:
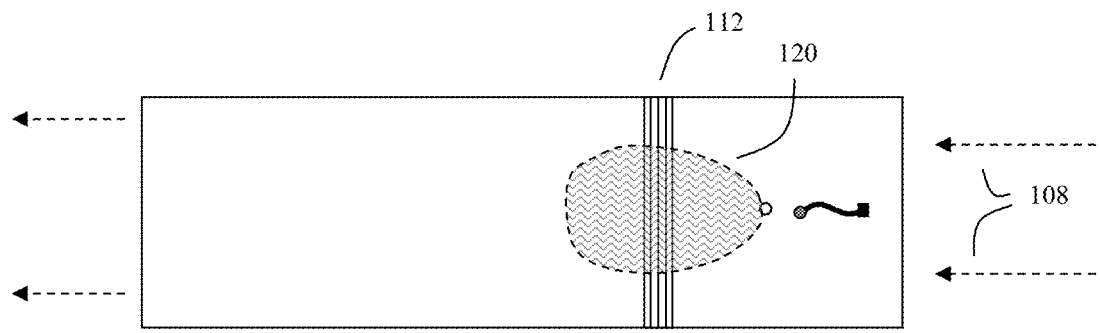
FIG. 4A shows how the system operates at higher flow rates, and with a color generating reagent.

FIG. 4A shows how the system operates at higher flow rates (108), and with a color generating reagent (106r). In this example, the mechanical flow meter is now dispersed downstream by the running water. In this example, assume that the reagent introduces a color change in the running water that varies as a function of a chemical impurity, but this color change does not cause an increase in turbidity. Here the optical targets (112) are still easy for the camera to see, even though the reaction zone (120).

Figure 4B:
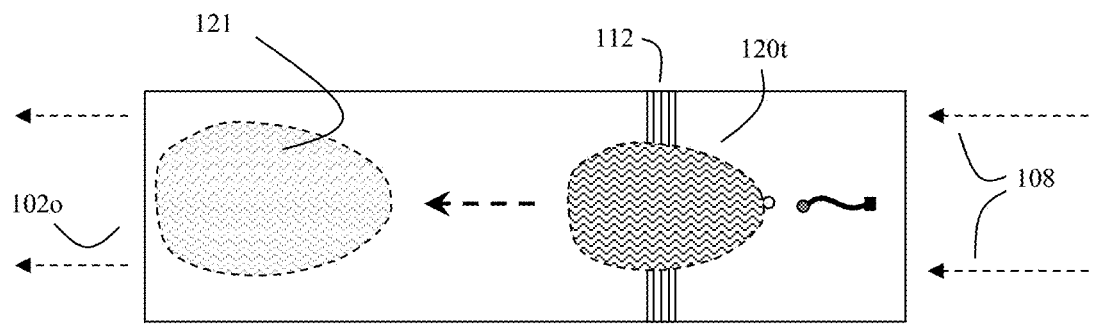
FIG. 4B shows how the system operates at higher flow rates, and with an agent that causes suspended solid particles in the water to form turbid aggregates.

FIG. 4B shows how the system operates at higher flow rates (108), and with an agent (106r) that causes suspended solid type impurities in the water to form larger aggregates. These aggregates show up as a region of higher turbidity (cloudy water) in the reaction zone (120t), and the amount of turbidity can be estimated by how much the turbidity (120t) blocks the optical targets (112).

Soon, often only a few seconds or less after the smartphone has imaged the reaction zone (120, 120t), the water flow (108) then carries the no longer needed (spent) reaction zone (121) out of the chamber's outlet (102o).

As previously discussed in U.S. Pat. No. 10,817,725, the entire contents of which are incorporated herein by reference, standard smartphones, such as Apple iOS smartphones, may be modified to provide additional information for environmental analysis.

FIG. 5 shows the rear of a smartphone (204), with a combination telescopic periscope (210) and optional spectrum dispersion device (220) mounted on a smartphone case (205) and attached over two (207, 208) of the smartphone's three video camera lenses (206, 207, 208).

Here, as previously discussed, one smartphone video camera system, such as (206) can be used to image the apparatus (100), and in particular window (102w), reaction zone (120), and water flow device (104). Here, a first video camera (206) may image the apparatus directly, while another video camera, such as (208) may employ a periscope (210) and/or optical filter (222) arrangement to help enable the system to better visualize the volume of the reaction zone (120) at any time, monitor any reaction with reagents, as well as to better differences in reflection as a function of angle, which can give turbidity information.

FIG. 5 also shows the smartphone case (205), as well as the light paths that incoming light takes as the light travels through the telescopic periscope (210), and through the spectrum dispersion device (220), and into the video camera lenses (208) and (207). Video camera and lens (206) are used to obtain normal (reference) images. Usually, video camera (206) will be the smartphone's telephoto lens camera, and additional (but optional) image magnifying lens arrangements are added to the telescopic periscope (210) and the light spectrum dispersion device (220) to obtain roughly equivalent magnification for all video cameras. The telescopic periscope attachment will typically contain angled mirrors to pass the signal from the far end of the periscope to the camera lens (208). In some embodiments, the telescopic periscope may be made extendible to extend still further away from lens (208) as desired.

FIG. 5A is a top view of the smartphone system previously shown in FIG. 5. Here an optional optical filter (222) is also shown. This optical filter can act to pass light of certain wavelengths or colors, while blocking light of other wavelengths or colors. This can help the system detect the level of chemical reaction in the reaction zone (120)

In a preferred embodiment, periscope attachment (210) will have a length of at least six inches and is configured to increase a spatial separation between the first viewpoint images and the second viewpoint images by at least six inches. In a preferred embodiment, the periscope attachment may further comprise a periscope lens arrangement, configured to adjust the magnification of the second viewpoint images to match the magnification of the first viewpoint images.

Figure 6:
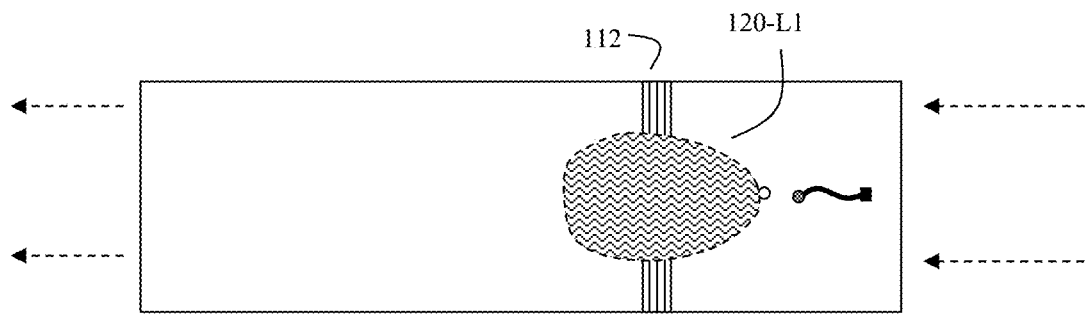
FIG. 6 shows the reaction zone photographed through a first video camera lens and a first optical filter.

FIG. 6 shows the reaction zone photographed through a first video camera lens and a first optical filter (or no filter), such as video camera (206). This view of the reaction zone is designated 120-L1.

Figure 6A:
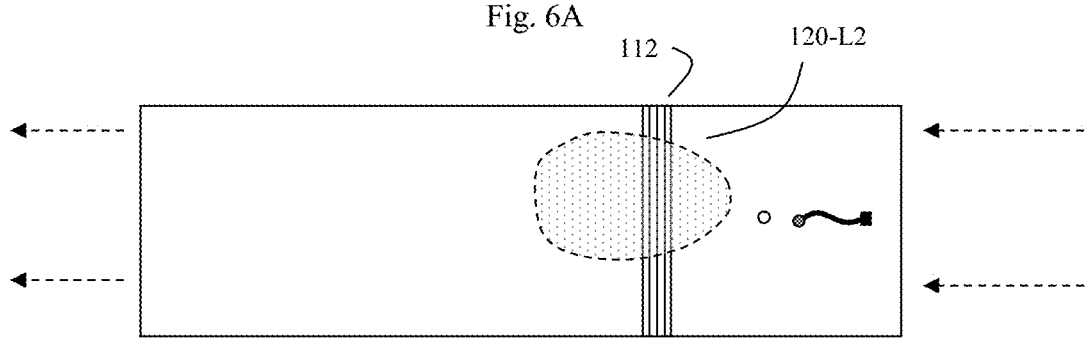
FIG. 6A shows the same reaction zone, at the same time, photographed through a spatially separated second smartphone video camera lens and a different optical filter.

FIG. 6A shows the same reaction zone, at the same time, photographed through a spatially separated second smartphone video camera lens and a different optical filter, such as video camera lens 208 and periscope and filter arrangement (210) and (222). This alternate view of the reaction zone is designated 120-L2.

Figure 6B:
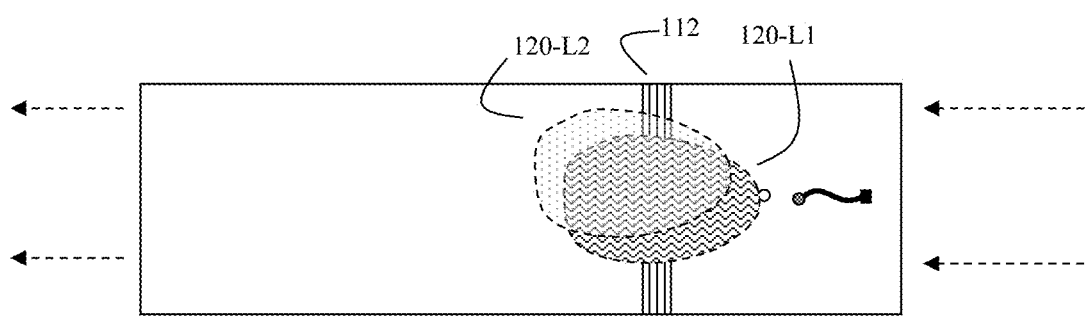
FIG. 6B shows image from FIG. 6 superimposed on the image from FIG. 6A, showing how this method provides further information about the spatial extent of the reaction zone, as well as the color and turbidity changes caused by the test reagent.

FIG. 6B shows the image from FIG. 6 (120-L1) superimposed on the image from FIG. 6A (120-L2), showing how this method provides further information about the spatial extent of the reaction zone, as well as additional information about the color and turbidity changes caused by the test reagent (106r). The differences in the shapes and position of the reaction zones (120-L1) vs (120-L2) can be used, with suitable stereo imaging algorithms, to better compute the volume of the reaction zone. Differences in color and ability to visualize the optical targets (112), between the two video cameras, can be used to obtain more precise information about the extent of the chemical reaction and turbidity in the reaction zone.

Figure 7:
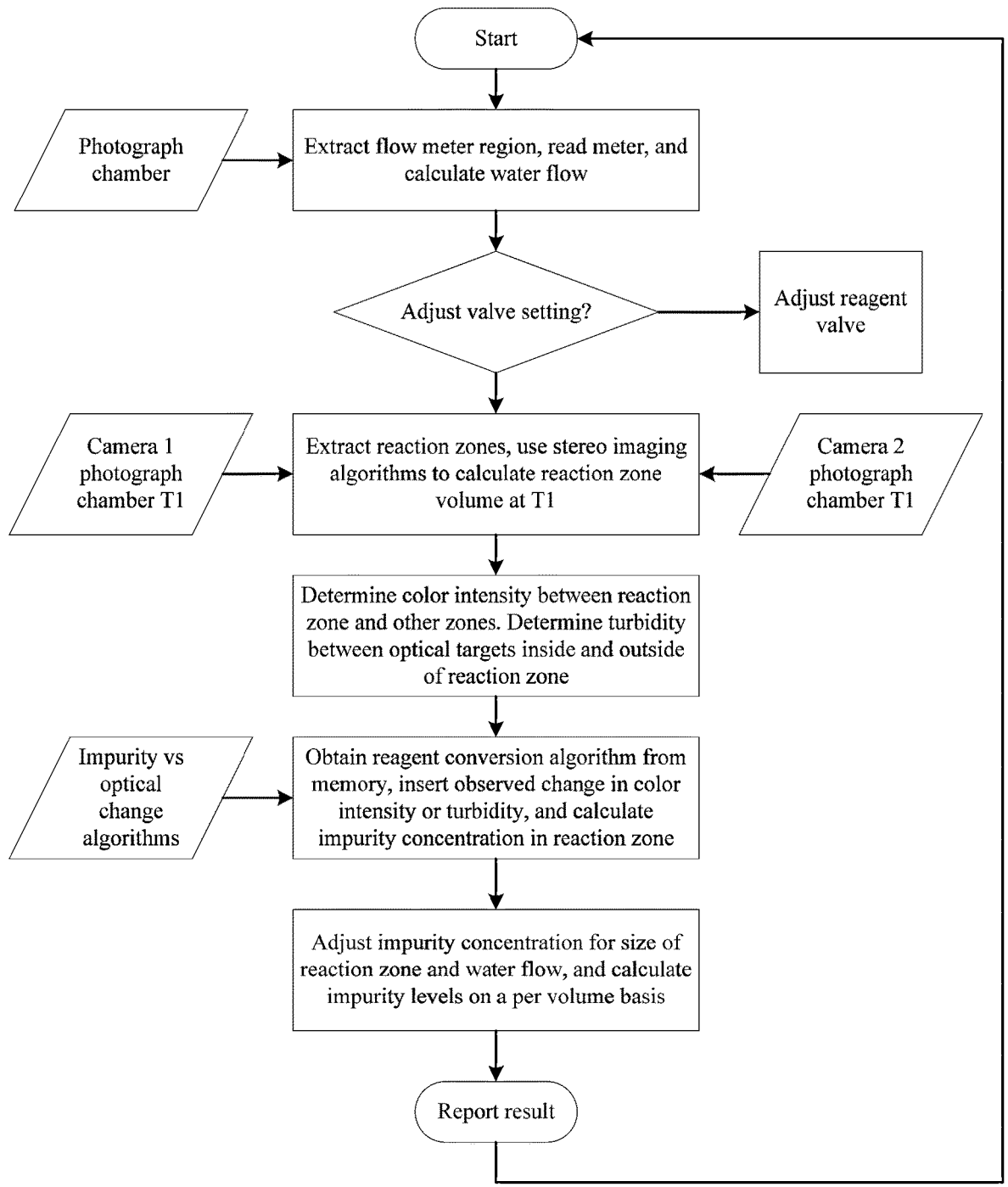
FIG. 7 shows a software flowchart showing how the smartphone's processor can operate according to one embodiment of the invention.

FIG. 7 shows a software flowchart showing how the smartphone's processor can operate according to one embodiment of the invention. Here "T1" is time 1.

As previously discussed, in some embodiments, the reagent dispensing system (106) contain reagent (106r) sufficient for a plurality of automatic administrations (indeed, with a sufficiently large container, reagent for hundreds or thousands of tests may be loaded). The processor can also be configured (see the loop between the beginning and the end of the flowchart in FIG. 7) so that after the system performs a first analysis, the system can then automatically implement various subsequent analysis as well. This allows the system to run unattended overnight, or even up to days or weeks at a time.

Also as previously discussed, in some embodiments, it will also be useful to configure the processor to compare the amount of impurity found in any given analysis against a maximum limit. This way, the processor can also be used to control an alarm system, or even a water shut-off valve, in the event that the detected impurities exceed this maximum limit.

The invention claimed is:

1. A method of analyzing running water for impurities, said method comprising:

placing a chamber comprising an inlet, an outlet, and at least one optically transmissive window in said water so that at least some of said water, comprising a sample of said water, enters said inlet, transits past said optically transmissive window, and exits said outlet while continuously flowing through said chamber;

said chamber further comprising a light reflective background disposed underneath said optically transmissive window and configured so that said running water runs between said optically transmissive window and said light reflective background while transiting said chamber;

said chamber further comprising a mechanical flow meter that produces a visible changing flow signal responsive to a flow rate of said sample of said water;

said light reflecting background comprising at least one region with a defined optical characteristic;

said chamber further comprising at least one reagent dispensing system configured to automatically administer, at a controlled rate, at least one reagent into said sample of said water while said water is transiting said chamber;

said at least one reagent selected to induce a change in the optical characteristics of said sample of said water in response to at least one impurity in said water;

exposing said chamber to light so that said light reflects off said light reflecting background, passes through at least some of said sample of said water, and exits said optically transmissive window;

using a smartphone comprising at least one processor and at least two spatially separated video cameras to simultaneously obtain, over a plurality of locations along said optically transmissive window, and a plurality of times while said water is transiting said chamber, said plurality of times spanning at least before and during automatic administration of said at least one reagent, color video images from at least two different camera angles, of said plurality of locations along said optically transmissive window;

said smartphone further comprising a lens attachment, said lens attachment configured to create any of an enhanced spatial separation between said spatially separated video cameras or a different optical filter between said spatially separated cameras;

and using said at least one processor to analyze said color video images from said spatially separated video cameras, to determine, based on said at least one reagent, and images of said plurality of locations along said optically transmissive window at said plurality of times, and said changes in said optical characteristics of said sample of water, at least one amount and type of impurity in said water.

2. The method of claim 1, further using said processor and said changing flow signal to determine a flow rate of said sample of said water; and
using said flow rate to configure the controlled rate of said one reagent dispensing system.

3. The method of claim 1, wherein said light is sunlight, and said light reflecting background comprises a white matte surface that reflects light uniformly over a plurality of angles.

4. The method of claim 1, wherein said at least one reagent induces a change in the color of said sample of said water in response to a fully dissolved impurity comprising any of chlorine, arsenic, heavy metal, or nitrate type impurity, and wherein light reflective background has at least one region with light reflecting background selected to facilitate detection of said change in said color;
wherein said at least one processor is configured to determine said at least one amount and type of impurity by analyzing color video images of locations both upstream of said reagent, and down stream of said reagent, and determining differences in at least the colors of said color video images between those locations upstream and downstream of said reagent.

5. The method of claim 4, wherein said different optical filter is selected to either preferentially absorb or preferentially pass wavelengths of light corresponding said at least one reagent's change in color, and wherein said at least one processor uses said different optical filter to further analyze said color images.

6. The method of claim 4, wherein said reagent comprises any of orthotolidine, resorufin b-D-glucronide, alum, polyethylene oxide or polyacrylamide.

7. The method of claim 1, wherein said at least one reagent induces a change in a turbidity of said sample of said water in response to suspended solids or colloids in said water;
and wherein light reflective background has at least one region with a light reflecting background selected to facilitate detection of said change in turbidity;
wherein said at least one processor is configured to determine said at least one amount and type of impurity by analyzing color video images of locations both upstream of said reagent, and downstream of said reagent, and determining differences in at least an opacity of said color video images between those locations upstream and downstream of said reagent.

8. The method of claim 7, wherein said at least one region contains a plurality of optical targets that become progressively harder to resolve as turbidity increases.

9. The method of claim 7, wherein said at least one region contains a plurality of reflective areas configured to reflect incident light through said sample of water at a plurality of different angles, where each different angle thus travels a different distance through said sample of water, and is attenuated by the turbidity of said sample of water by a differing extent;
wherein said lens attachment is configured to create a variable spatial separation of at least six inches between said spatially separated video cameras;
and using said at least one processor to analyze said color video images from said spatially separated video cameras, to determine, based on said at least one reagent, and images of said plurality of locations along said optically transmissive window at said plurality of times, and said changing flow signal, at least one amount of suspended solids or colloids in said water.

10. The method of claim 7, wherein said light is any of sunlight or artificial light, and said at least one reagent comprises flocculant selected to accelerate a rate of flocculation of any suspended solid or colloidal impurities in said water, thereby causing an increase in turbidity in those portions of water downstream of said reagent.

11. The method of claim 1, further using said smartphone to analyze images of said mechanical flow meter, and to use said images to produce said flow signal responsive to a flow rate said water.

12. The method of claim 1, further using said processor to compare said determination against a preset maximum limit of said amount of impurity, and to automatically control any of an alarm system or a water shut-off system when said amount of impurity exceeds said preset limit.

13. The method of claim 1, wherein said reagent dispensing system is configured to contain reagent sufficient for a plurality of automatic administrations, wherein after a given said determination of said at least one amount and type of impurity in said water is performed, then using said processor to automatically implement a next determination said at least one amount and type of impurity in said water.

14. A method of analyzing running water for impurities, said method comprising:

placing a chamber comprising an inlet, an outlet, and at least one optically transmissive window in said water so that at least some of said water, comprising a sample of said water, enters said inlet, transits past said optically transmissive window, and exits said outlet while continuously flowing through said chamber;

said chamber further comprising a light reflective background disposed underneath said optically transmissive window and configured so that said running water runs between said optically transmissive window and said light reflective background while transiting said chamber;

said chamber further comprising a mechanical flow meter that produces a visible changing flow signal responsive to a flow rate of said sample of said water;

said light reflecting background comprising at least one region with a defined optical characteristic;

said chamber further comprising at least one reagent dispensing system configured to automatically administer, at a controlled rate, at least one reagent into said sample of said water while said water is transiting said chamber;

further using a smartphone comprising at least one processor, and at least two spatially separated video cameras, said processor and said visible changing flow signal to determine a flow rate of said sample of said water;

using said flow rate to configure said controlled rate of said one reagent dispensing system;

said at least one reagent selected to induce a change in the optical characteristics of said sample of said water in response to at least one impurity in said water;

exposing said chamber to light so that said light reflects off said light reflecting background, passes through at least some of said sample of said water, and exits said optically transmissive window;

using said smartphone and said at least two spatially separated video cameras to simultaneously obtain, over a plurality of locations along said optically transmissive window, and a plurality of times while said water is transiting said chamber, said plurality of times spanning at least before and during automatic administration of said at least one reagent, color video images from at least two different camera angles, of said plurality of locations along said optically transmissive window;

said smartphone further comprising a lens attachment, said lens attachment configured to create any of an enhanced spatial separation between said spatially separated video cameras or a different optical filter between said spatially separated cameras;

and using said at least one processor to analyze said color video images from said spatially separated video cameras, to determine, based on said at least one reagent, and images of said plurality of locations along said optically transmissive window at said plurality of times, and said changes in said optical characteristics of said sample of water, at least one amount and type of impurity in said water;

wherein said reagent dispensing system is configured to contain reagent sufficient for a plurality of automatic administrations, wherein after a given said determination of said at least one amount and type of impurity in said water is performed, then using said processor to automatically implement a next determination said at least one amount and type of impurity in said water; and further using said processor to compare said determination against a preset maximum limit of said amount of impurity, and to automatically control any of an alarm system or a water shut-off system when said amount of impurity exceeds said preset limit.

15. The method of claim 14, wherein said at least one reagent induces a change in the color of said sample of said water in response to a fully dissolved impurity comprising any of chlorine, arsenic, heavy metal, or nitrate type impurity, and wherein light reflective background has at least one region with light reflecting background selected to facilitate detection of said change in said color;

wherein said at least one processor is configured to determine said at least one amount and type of impurity by analyzing color video images of locations both upstream of said reagent, and downstream of said reagent, and determining differences in at least the colors of said color video images between those locations upstream and downstream of said reagent.

16. The method of claim 14, wherein said at least one reagent induces a change in a turbidity of said sample of said water in response to suspended solids or colloids in said water;

and wherein light reflective background has at least one region with a light reflecting background selected to facilitate detection of said change in turbidity;

wherein said at least one processor is configured to determine said at least one amount and type of impurity by analyzing color video images of locations both upstream of said reagent, and downstream of said reagent, and determining differences in at least an opacity of said color video images between those locations upstream and downstream of said reagent.

* * * * *